United States Patent
Ringold (10) Patent No.: US 8,969,022 B2
(45) Date of Patent: Mar. 3, 2015

(54) METHOD AND SYSTEM FOR DETECTING LYMPHOSARCOMA IN CATS USING BIOMARKERS

(71) Applicant: Veterinary Diagnosis Institute, Inc., Simi Valley, CA (US)

(72) Inventor: Randy Ringold, West Hills, CA (US)

(73) Assignee: Veterinary Diagnostics Institute, Inc, Simi Valley, CA (US)

( * ) Notice: Subject to any disclaimer, the term of this patent is extended or adjusted under 35 U.S.C. 154(b) by 0 days.

(21) Appl. No.: 13/672,687

(22) Filed: Nov. 8, 2012

(65) Prior Publication Data

US 2014/0127711 A1    May 8, 2014

(51) Int. Cl.
| | | |
|---|---|---|
| *G01N 33/573* | (2006.01) | |
| *G01N 33/566* | (2006.01) | |
| *C12Q 1/00* | (2006.01) | |
| *G01N 33/574* | (2006.01) | |

(52) U.S. Cl.
CPC .... *G01N 33/57488* (2013.01); *G01N 33/57426* (2013.01)
USPC ................................. 435/7.4; 436/501; 435/4

(58) Field of Classification Search
CPC ........................... G01N 33/573; G01N 33/566
USPC ............................................ 435/7.4; 436/501
See application file for complete search history.

*Primary Examiner* — Rodney P Swartz
(74) *Attorney, Agent, or Firm* — Karim Lagobi (57) ABSTRACT

The invention provides a method and system for developing and using diagnoses of lymphosarcoma in feline subjects using thymidine kinase (TK) and haptoglobin (HP) as biomarkers. The invention provides a method for obtaining the level of each biomarker and computing an index for a feline subject. The invention provides predefined index ranges to which the index value may be matched in order to determine whether the subject has a high probability of being affected by lymphosarcoma, even when the subject shows apparent symptoms that may be common with inflammatory bowel disease.

1 Claim, 5 Drawing Sheets

METHOD AND SYSTEM FOR DETECTING LYMPHOSARCOMA IN CATS USING BIOMARKERS

FIELD OF THE INVENTION

The invention relates to detecting cancer in feline; and particularly the invention provides a method and system for constructing a diagnosis for cancer in feline using a plurality of biomarkers, and further using the diagnosis to differentiate between cancer and other affections regardless of the similarity in the apparent symptoms, and detect the propensity of a subject to develop cancer.

BACKGROUND OF THE INVENTION

The level of biomarkers in body fluids is used in the process of detecting numerous health affections. Measuring the level of one or more specific biomarkers in the blood is typically a fast and relatively inexpensive means for diagnosing a disease or leading to the diagnosis thereof before prescribing other (more expensive and/or time consuming) tests such as radiological, cytological, histological and immunological tests etc.

However, many challenges face a medical (or veterinary) practitioner in selecting a panel of biomarkers to be tested for any specific case, and then in interpreting the results of the measured level of each biomarker in view of the symptoms the patient is exhibiting. The symptoms are generally only broad indicators of any particular disease, since some diseases, such as infection-related diseases, trigger symptoms in a patient at the onset of the disease or shortly thereafter, while other diseases, such as many types of cancer, trigger symptoms a considerable time after a tumor starts to develop. Diagnosing the underlying disease often requires testing for a panel of biomarkers, where some tests may be conducted to confirm a suspicion of a disease, while other tests may be conducted to rule out one or more other diseases.

Along with the challenge of choosing the panel of biomarkers for testing, there is the challenge of interpreting the test results. Some biomarkers are proven to be tightly correlated with the presence of a certain disease, while other biomarkers provide only a probability level a patient has a particular disease. For example, in humans sustained hyperglycemia is a good indicator of diabetes, while, for example, in dogs an increased level of thymidine kinase above a given threshold is an indicator of Hemangiosarcoma, which should be confirmed through histology.

Moreover, screening, diagnosing and/or monitoring a disease may involve any number of tests. According to existing methods and systems, when using biomarkers the broader are the symptoms, the more tests are carried out. A practitioner uses his/her own experience to interpret the test results when using biomarkers to detect a disease, to follow the progression of a disease and/or to monitor the result of a treatment. The latter introduces a level of subjectivity in diagnosing test results, which may cause discrepancies between interpretations by the same person over time, among practitioners and even among entire health institutions.

Therefore, there is a need for a method and system for selecting a set of biomarkers and developing a method of use for detecting one or more target diseases and differentiating between the diseases to help a practitioner interpret the test results and potentially reveal the underlying affection or the propensity of a patient to develop a given disease.

SUMMARY OF THE INVENTION

The invention provides a method and system for constructing and using a diagnosis that reveals whether in a feline patient is affected by cancer using a plurality of biomarkers, and further using the diagnosis to differentiate between the underlying health affections regardless of the commonality of symptoms.

Constructing a diagnosis following the invention involves selecting a set of biomarkers known for their relation with cancer, and measuring the level of the biomarkers in a group of subjects. The invention teaches how to compute a numerical value, i.e. an index, using the biomarker levels, then define ranges of the index on a scale, where each range may be matched with a subgroup of subjects segregated on the basis of their health status. Provided the latter method of segregation of subjects by health status, a practitioner may subsequently utilize the index scale to diagnose a health affection in a patient by measuring the level of the biomarkers in the patient, then computing an index value for the patient and matching the value to the predefined index scale to determine whether the patient is likely affected by cancer or sepsis.

A system according to the invention may be implemented as a computer program configured to receive input data (e.g., biomarker data and health status data etc.), and determine ranges for a particular diagnosis. The computer system may also receive the input for a particular patient, compute the index value and output the result of the diagnosis. The system may stand alone or be embedded in any diagnosis machine.

With state of the art practices, practitioners are faced with the difficulty of interpreting the results of biomarker data, particularly when comparing the progress of a disease, such as while monitoring a subject with a particular propensity of having a disease, or monitoring the health progress of patients following a treatment. The invention provides the latter practitioners tools for diagnosing an underlying health affection and monitoring the progress of a disease using numerical indicators for any particular situation.

The invention teaches using a two-biomarker neoplasia index to detect the occurrence of lymphosarcoma in cats. Using thymidine kinase and haptoglobin as biomarkers, the invention provides a means to detect whether a patient has a high probability of having lymphosarcoma.

The invention provides means to detect and differentiate between subjects having lymphosarcoma (LSA) versus subjects affected by inflammatory bowel disease (IBD) or normal subjects. A cat having either Lymphosarcoma or inflammatory bowel disease may present common visible symptoms which may lead a practitioner to an inconclusive diagnosis using those symptoms alone. The biomarker approach, as taught by the invention, allows a practitioner to determine a high likelihood of lymphosarcoma or inflammatory bowel disease in a subject showing common visible symptoms.

DETAILED DESCRIPTION OF THE INVENTION

The invention provides a method and system for detecting disease in animals and humans. The invention provides a method and system for developing and using a diagnosis targeting a particular one or more health conditions using a plurality of biomarkers, and further using the diagnosis to differentiate between several affections that may trigger similar health symptoms in a patient. Furthermore, the method and system according to the invention may be used to determine the propensity for an individual to develop a disease (e.g., one or more types of cancer), providing a practitioner the means for detecting a disease before the symptoms are visible and/or monitoring a disease post treatment.

The disclosure presents a method and system for diagnosing a feline subject presenting general inflammation symptoms, whether the subject is affected by lymphosarcoma or inflammatory bowel disease using two biomarkers.

In the following description, numerous specific details are set forth to provide a more thorough description of the invention. It will be apparent, however, to one skilled in the pertinent art, that the invention may be practiced without these specific details. In other instances, well known features have not been described in detail so as not to obscure the invention. The claims following this description are what define the metes and bounds of the invention.

Portions of the methods and systems disclosed in the present disclosure have been disclosed in co-pending patent application Ser. No. 13/672,677 and co-pending patent application Ser. No. 13/672,649.

TERMINOLOGY

Throughout the description, the terms individual, subject or patient may refer to an animal subject or a person whose biological data are used to develop and/or use an implementation of the invention. The subject may be normal (or disease-free) or showing any level of symptoms.

The term biomarker refers to any indicator in any body part (e.g., bodily fluid or tissue) that may be collected and the presence of which measured through any of its manifestations such as enzymatic activity, mass, concentration, cell count, cell shrinkage/shape, deoxyribonucleic acid (DNA) and/or ribonucleic acid (RNA) genetic level of expression or any aspect of the biochemical or the physiological markers that may be related to one or more health conditions. Moreover, for the purpose of designing health status indices (see below) a biomarker data may be any related data that may be considered for diagnosing a disease (or the probability of occurrence thereof) such as age, sex, any biometric data, genetic history (e.g., parent's health status or presence of any affection in the family) or any other data that may contribute to the diagnosis of a disease.

The term "index" is used throughout the disclosure to refer to a dependent variable that is calculated using two or more data inputs such as the level of a biomarker in the blood stream. A "neoplasia index" refers to an index that is computed with the goal of classifying subjects into groups based on cancer status. For example, a subject that may be apparently healthy (e.g., showing no signs of cancer), diagnosed with a malignant or a benign cancer or in any health status with regard to cancer, would have a neoplasia index value that reflects the health status, in accordance with embodiments of the invention.

The term "user" may be used to refer to a person, machine or a computer program acting as or on behalf of a person.

GENERAL CONCEPT OF THE INVENTION

The main concept of the invention is that by selecting a set of biomarkers and measuring their levels in an animal or a human subject, it is possible to compute a numerical value, i.e. an index, using those levels, and to compare the index value to a predefined scale that characterizes the health status of the subject using index ranges. The scale may define two or more ranges of the index values, wherein each range indicates a level of one or more diseases. For example, in a subject showing general symptoms of inflammation, a predefined scale may define two or more ranges that may indicate the presence of cancer, an infection, both cancer and infection or other diseases.

The invention teaches developing any particular diagnosis by selecting a set of biomarkers, then measuring the level of each biomarker from each individual of a sample group of subjects. In addition, other diagnoses (e.g., cytological, histological and physiological tests, physical examination etc.) are carried out on the subjects to accurately establish the health status of each subject.

According to embodiments of the invention, the biomarkers data serve to compute the index values, while the health status data serve to define two or more health status categories (e.g., healthy, cancer, benign tumor, infection etc.). Ranges of index values are then defined providing efficient segregation of subjects into the two or more health status categories.

Subsequently, to provide a diagnosis to a patient, a set of biomarkers according to a particular diagnosis is collected and measured, then an index value is computed using the test data, and the index value is compared to the predefined index scale to match a health status category, which reveals the patient's health status.

Figure 1:
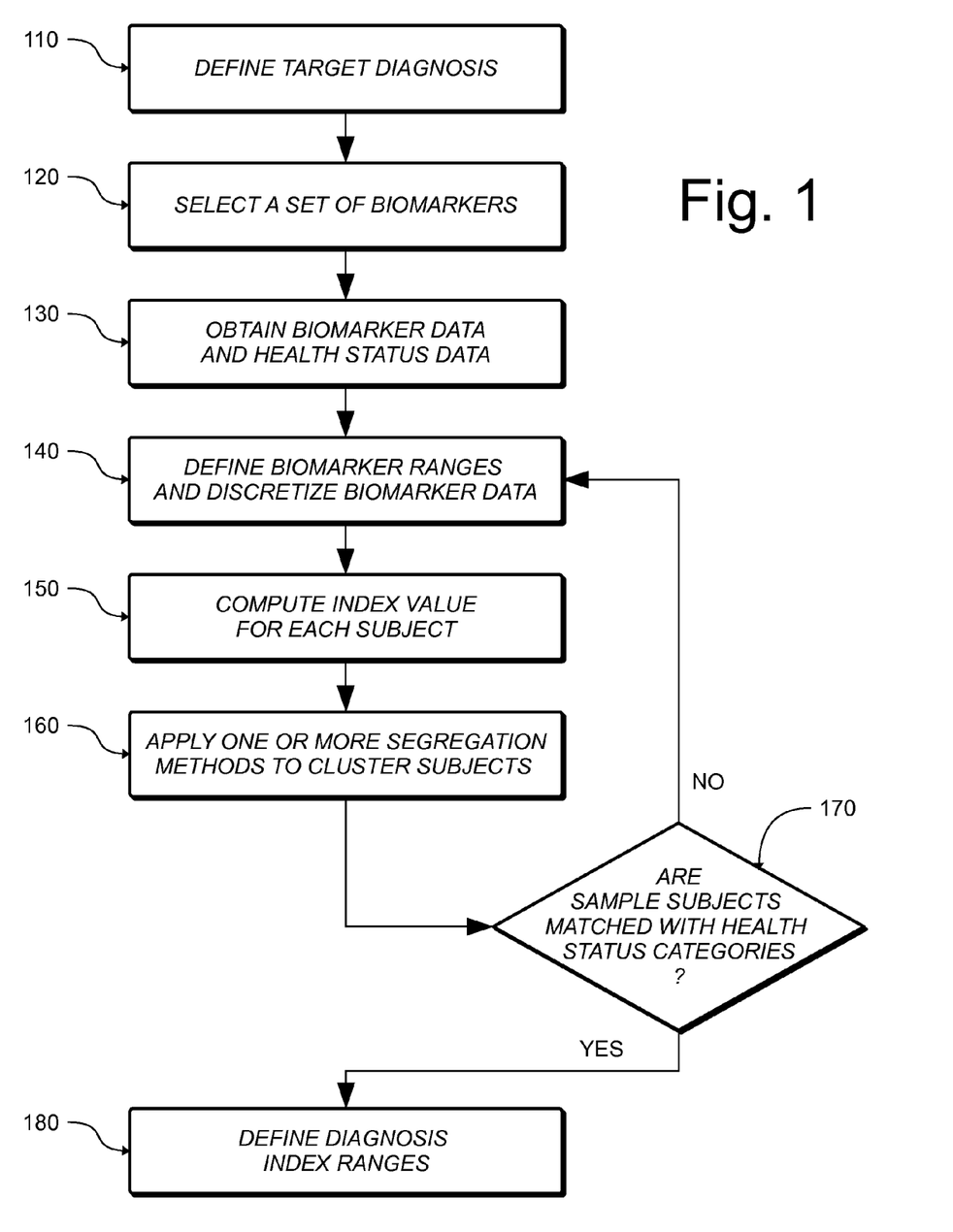
FIG. 1 is a flowchart diagram representing steps involved in developing a method for detecting and/or differentiating one or more target diseases, in accordance with an embodiment of the invention.

FIG. 1 is a flowchart diagram representing steps involved in developing a method for detecting and/or differentiating one or more target diseases, in accordance with an embodiment of the invention. Step 110 represents defining a target diagnosis. A typical target diagnosis involves defining a disease (e.g., Infection, any type of Cancer etc.) or two or more diseases that may or may not display common symptoms. Any prior knowledge with regard to the target disease(s) may be considered, thus, the symptoms that accompany the disease, the severity of the symptoms, the speed at which the symptoms develop and any other aspect of the disease profile may be considered to define the target diagnosis.

Step 120 represents selecting a set of biomarkers for use in the diagnosis. Selecting a set of biomarkers may be based on previous knowledge of a correlation (be it positive or negative) between the level of a given biomarkers and the presence (or absence) of the one or more target diseases. For example, thymidine kinase may be used as a biomarker to detect any type of cancer since thymidine kinase is typically present in the cells undergoing cell division, which is the case of cancerous cells.

Step 130 represents collecting data from a group of subjects. The group of subjects may be a sample of subjects comprising normal subjects (i.e. healthy) showing none of the symptoms defined in Step 110, and affected subjects showing any level of severity of those symptoms. Bodily fluids, tissue or any other body sample may be appropriately collected in order to measure the level of each biomarker of the set of biomarkers defined at step 120.

In addition, the subjects undergo a plurality of tests, such as histological, radiological tests or any other test designed to establish the presence or absence of the target disease(s). Other tests may be conducted on each subject to either further confirm the disease or rule out other diseases that may share common symptoms.

Moreover, other non-disease related data may also be considered. The latter data comprise age, sex, any biometric data, genetic history (e.g., parent's health status or presence of any affection in the family) or any other data that may contribute to the diagnosis of a disease.

The outcome of step 130 is a set of data points that characterizes each subject individual data and its level of each biomarker in the set of data, and a health status that establishes whether each subject is a non-carrier or a carrier of one or more diseases and eventually the stage (or severity) of each disease. For example, when considering cancer, a subject may be classified as non-carrier of cancer, having a benign tumor, an early cancer stage or advanced cancer stage, and any given type of cancer. In the latter example, the set of biomarkers may comprise thymidine kinase, C-reactive protein and/or any other biomarker selected at step 110 to include in the development of the diagnosis method. The level of each biomarker may be expressed in any unit that characterizes the presence of the biomarker in the body. Thus, an enzyme may be characterized by the level of its enzymatic activity, a protein, a hormone or any other biomarker may be expressed by a concentration level such as its mass or moles per volume of tissue or bodily fluid.

Step 140 represents the process of finding range values for each biomarker. For example, when considering thymidine kinase as a biomarker for cancer, a first range of zero units per liter (0 U/l) through five units per liter (5 U/l), a second range of five units per liter (5 U/l) through eight units per liter (8 U/l), and a third range of eight units per liter (8 U/l) and above may be defined as ranges for that specific biomarker.

Step 140 also involves discretizing the data, which comprises attributing a score number to each previously defined range of a biomarker level. Using the example of the three (3) thymidine kinase ranges above, the first range may be attributed the value zero (0), the second range may be attributed the value one (1) and the third range may be attributed the value two (2).

The discretization may be carried on other non-disease related data such as age. In the latter example, age may be selected for the diagnosis as a factor in the increase of the probability of having a target affection. Thus, age may be discretized such that a person of 0 to 20 years of age is attributed a value of "0", a person of 20 to 40 years of age may be attributed a value "1" and a person over 40 years of age may be attributed a value of "2". Sex may be discretized as "1" and "0" for female and male, respectively.

Step 150 represents computing an index value for each subject as follows:

$$I = \sum_{i=1}^{i=N} C_i \cdot L_i \quad (1)$$

where the index value "I" for each subject may be the sum of the product of the score level "L" (e.g., computed at step 140) and a coefficient "C" associated with the "$i^{th}$" data input for a number "N" of data inputs (e.g., biomarker level, age, biometric data etc.). The coefficient "C" may be determined empirically as shown below at steps 160 and 170.

Step 160 represents applying one or more methods for segregating subjects using the health status data and the computed index values. For example, the method of segregation may be the Receiver Operating Characteristic (ROC) curve analysis. ROC curve analysis is a well known method in the medical field for determining whether a correlation between the level of a biomarker may serve as an indicator of the presence of a health condition. The latter is possible for example when there is a strong correlation between the amount of a substance in the body (e.g., high cholesterol) and a health condition (e.g., sclerosis of blood vessels).

Using the ROC curve analysis on the index values of all subjects in the group, it is possible to determine whether there is a cutoff value capable of classifying individuals into groups matching their health status. For example, if subjects carrying a disease are labeled as positive and the non-carriers are labeled as negative, the ROC curve analysis may yield a threshold that classifies the subjects into an above and a below-threshold groups matching the health statuses carrier and non-carrier of the disease, respectively. There may be false positives and false negatives for each chosen cutoff value in the range of possible values. The rate of success in determining true positive cases is called "Sensitivity", whereas the rate of success in determining true negative cases is called "Specificity". Sensitivity and specificity for a plurality of cutoff values are computed. Sensitivity and Specificity are rates, and thus may be expressed in the range of zero (0) to one (1), or as a percentage from zero (0) to one hundred percent (100%). The results are plotted as Sensitivity values versus one (1) (or 100% depending on the unit of choice) minus the corresponding specificity. The area under the curve (AUC) reveals whether ROC analysis may be a valid classifier of the data: the closer the AUC is to 100%, the better classifier is the ROC analysis. On the contrary, the ROC analysis may not be considered for classification purposes if the AUC is closer to 50%, which is considered close to a random process. In general, the ROC method of analysis may be considered valid, if the AUC is at least 0.8.

Moreover, each threshold value yields a "Sensitivity" and "Specificity". In populations where where ROC analysis appears adequate, the "Sensitivity" curve decreases as the "Specificity" increases. At a particular threshold, the apex, the total of Sensitivity and Specificity is at a maximum. The apex is typically chosen as the threshold of classification if it yields a Sensitivity and Specificity each above 0.85, otherwise a threshold for Specificity and a threshold for Sensitivity may be respectively selected to yield a success rate of at least 0.85.

ROC analysis is one of any existing methods that may be utilized in embodiments of the invention to detect clusters in the data that define the clustering boundaries capable of segregating subjects into groups matching health status categories. For example, k-means clustering, hierarchical clustering, neural networks or any other clustering clustering method may be utilized in one or more embodiments of the invention. Furthermore, an embodiment of the invention may conduct the steps of FIG. 1 using a plurality of methods of clustering the data to achieve the results of the invention. The final clustering method that may be retained in any particular embodiment of the invention may be the one that yields the highest success rate of the diagnosis.

Step 170 represents computing success scores of the method of segregating of subjects in the test group. If the success level of the segregation into health categories is not satisfactory (e.g., no statistical difference compared to a population drawn from a random process), the parameters for computing the index values are revised and the analysis is repeated at step 140. The process of searching for optimal parameters may be repeated until the result of classification of subjects reaches (or exceeds) an acceptable success rate. Otherwise, if no optimal parameters may be found, the result may indicate that the chosen set of biomarkers is unsuitable for segregating the subjects based on the index method into the proposed health status categories.

The search for optimal parameters may involve changing one or more boundary values for discretizing biomarker values, and/or the weight coefficients associated with each biomarker in computing the index value for each subject. The search method may be manual i.e. an expert practitioner may set the initial parameters and adjust them, through multiple iterations of computation, while considering the outcome of the success rate of classification of subjects into health status categories. Implementations of the invention may also use numerical methods for automatic search to optimize parameters. Such methods comprise brute force search, where a large number of values of parameters and combinations thereof are tested. The numerical methods for determining optimal values may use gradient descent search, random walk search or any other mathematical method for searching for optimal parameters in order to achieve the goal of maximizing the success rate of the classification of subjects into correct corresponding health status categories.

Computer programs for conducting a search, in accordance with an implementation of the invention, require ordinary skills in the art of computer programming. Moreover, existing computer programs may be adapted (through a programming scripting language) to carry out a search process in an implementation of the invention. Computer programs include such programs as Mathematica™, Matlab™, Medcalc™, or any other available computer program may be used.

Step 180 represent the final step of determining the final parameters (or range thereof) that may be used in a diagnosis of the target disease(s). The optimal parameters include the coefficient associated with each biomarker, the number of ranges and the boundary values that define the ranges for each biomarker. Step 180 also includes determining the index range boundaries that define the categories as defined by the health status of subjects. The latter parameters may be used in systems for diagnosing whether a subject is a carrier of the a disease, as will detailed below in the method of use.

The invention provides a means for facilitating the display and read out of the results by defining the boundaries between ranges as discrete values for ease of use. For example, a scale comprising two health statuses, such as "disease present" and "disease not present", may be defined has having a discrete boundary, such as one "1", where the scale range lower than "1" may be mapped to "disease not present" status, while the scale range greater than "1" is mapped to "disease present" status.

Defining range boundaries as discrete values may be carried out during the search for the optimal parameters (as described above). The discrete range boundary values may also be provided computationally (e.g., using multipliers and offsets) subsequent to determining the optimal parameters.

Figure 2A:
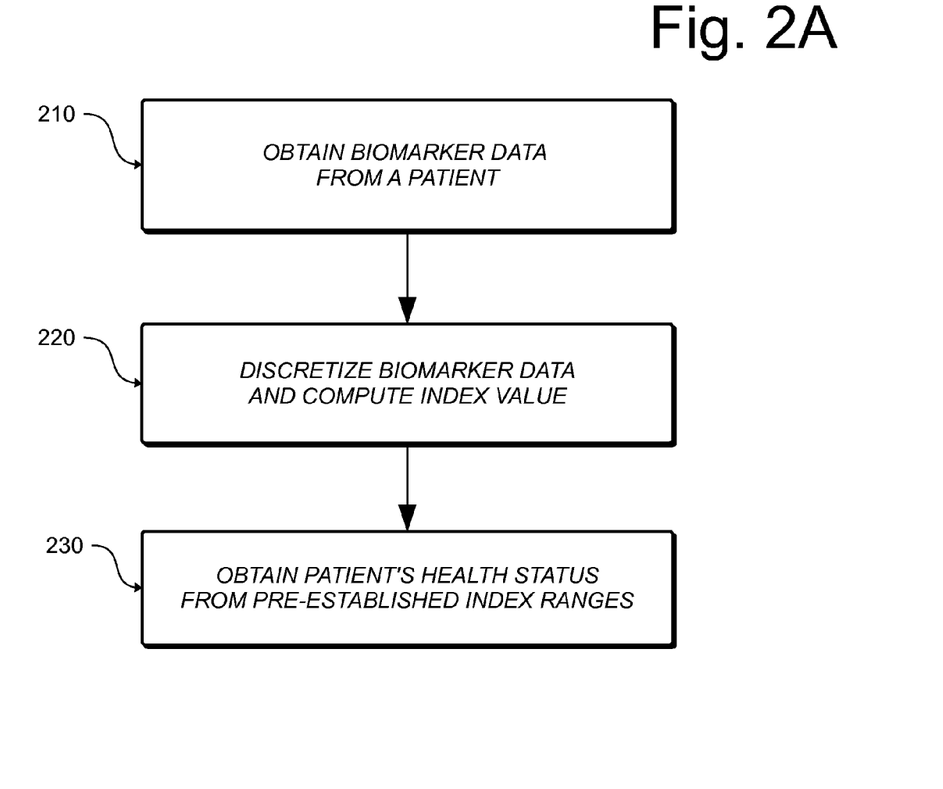
FIG. 2A is a flowchart of method steps involved in using a set of biomarkers in a diagnosis of one or more health statuses, in accordance with an implementation of the invention.

FIG. 2A is a flowchart representing method steps involved in using a set of biomarkers in a diagnosis of one or more health statuses, in accordance with an implementation of the invention. Provided a set of pre-established optimal parameters that yield an acceptable success rate for classifying subjects into health categories based on a computed index from biomarkers, the invention provides a method and system for testing whether a new patient is likely a carrier of a suspected disease using biomarkers. Step 210 represents obtaining data from a patient. Similarly to step 130 and depending on the specific set of biomarkers involved in a diagnosis, bodily fluids, tissue and any other data necessary for the diagnosis are collected and the level of each biomarker is assessed.

Step 220 represents computing an index value for the patient. Provided the discretization boundary values for each biomarker, the level of each biomarker is converted into a score value, and provided the coefficient associated with each biomarker, the index value for the patient may be computed using equation (1).

Step 230 represents determining a patient's health status group. The patient's computed index value is compared to that of the established boundary values for health status categories. As described above, the established mapping between index values allows for ascertaining the health condition of a patient using its own index value.

Figure 2B:
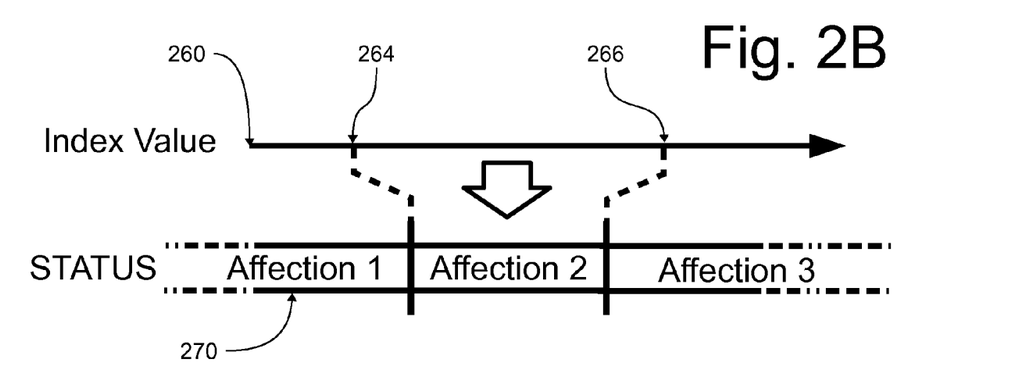
FIG. 2B is a graphical representation of a continuous index scale and defined index ranges corresponding health statuses as taught by the invention.

FIG. 2B is a graphical representation of a continuous index scale and defined index ranges corresponding to health statuses as taught by the invention. Line 260 represents a continuous scale of index values. Health status scale 270 represents the health status categories for which the diagnosis method was initially developed in accordance with the teachings of the invention. The health status scale may define two (2) or more health statuses, such as, in the case of cancer, non-carrier, benign tumor carrier and cancerous tumor carrier. Index values 264 and 266 may define the boundaries to read out the health status of a patient in question. Thus, a patient's index value that is less than about boundary 264 would indicate the patient in question is in a first health status category, an index value greater than about boundary 264 and less than about boundary 266 would indicate the patient is in a second health category while an index value greater than boundary 266 would indicate that the patient is in a third health status category. For example, a patient's index value may be within the range that matches the group of non-carriers of cancer, or the group of carriers of a benign tumor or the group of carriers of cancer.

The method steps as described in FIGS. 1, 2A and 2B may be carried out manually, i.e. a user may collect the data, compute the index value, then compare the the index value to a pre-defined set of ranges to obtain the health status category of a patient and/or the method steps may be implemented in a machine (e.g., digital computer) that carries out any or all of the steps of obtaining the data, computing the index value, obtaining the health status category and displaying/communicating the health status category to a user.

An embodiment of the invention may be implemented in a way where the biomarkers data considered for developing a target diagnosis are collected in (healthy) subjects showing no symptoms of the target affection. By monitoring the subjects over time and determining which subjects develop an ailment, the invention allows for building a diagnosis (or a predictor index) for revealing the propensity of a subject to develop a target affection in a future time based on current biomarker data.

The benefits of developing an index-based scoring system, in accordance with one or more implementations of the invention, are numerous. The teachings of the invention allow a practitioner to compare results obtained from different individuals using a plurality of data combined in an index. For assessing progress in an individual (e.g., monitoring health condition during or post-treatment), a practitioner may conduct the tests using several biomarkers and follow the variations of the index values. For assessing the risk factors for an individual to develop a given disease, a practitioner may determine a range of index values and/or a variation thereof over time that may be indicative of the development of the disease. For example, some dog breeds are more susceptible than others to developing certain types of cancer. The index values provided by a diagnosis, in accordance with an implementation of the invention, may be utilized to spot those individuals that may be in the process of developing a cancer at an early stage.

Moreover, since a plurality of implementations of the invention may be developed for the diagnosis/detection of various aliments, a patient may be subjected only once to a test of a superset of biomarkers that would include biomarkers from several target diagnoses. By measuring the level of various biomarkers, more than one index may be computed at any time. The result is that each patient may be represented in a multidimensional space of indices that characterizes the state of the patient. Thus, a practitioner is provided a means to assess the probability for the patient to have one ailment versus another ailment when both present common symptoms.

System for Developing and Using a Multi-Biomarker Index

Figure 3:
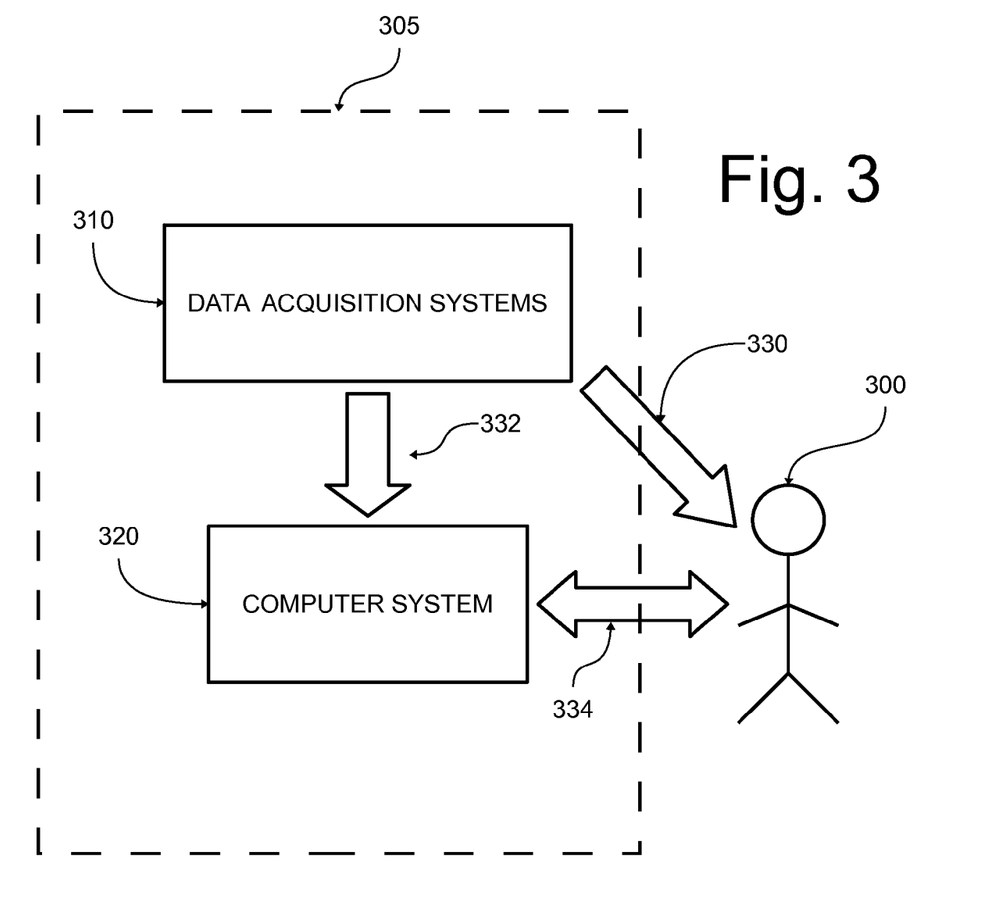
FIG. 3 is a block diagram representing components involved in the implementation of an embodiment of the invention.

FIG. 3 is a block diagram representing system components for implementing the development of use of diagnoses in accordance with an embodiment of the invention. The invention teaches the method steps described in FIGS. 1 and 2 as a general implementation of the development and use of diagnostic indices for any one or more target health affections in humans and/or animals. Furthermore, the invention teaches two-biomarker and three-biomarker methods for segregating feline subjects into groups affected by cancer, sepsis, SIRS. A system implementing an embodiment of the invention comprises one or more components for collecting data, one or more components for analyzing data, one or more components for communicating data with users.

Block 310 represents the data acquisition layer of any system that implements an embodiment of the invention. The system may be any system required for the acquisition of the biological data that may be associated with any particular target health affection for diagnosis or the development of a diagnosis thereof. For example, the biological data may require the measurement of the level of a particular substance in the blood (or in any other bodily fluid) and/or in an organ tissue. The substance may be a protein, a peptide, any type of hormone or any other molecule or ion the measurement of which may be relevant to the diagnosis of a particular health affection or the development of diagnosis thereof. In the case where a biomarker is a biological substance, Block 310 represents the necessary laboratory equipment for collecting biological samples and processing the samples in order to obtain the biological data required for a particular embodiment of the invention. For example, measuring a protein level in the blood requires many steps comprising collecting blood from subjects, separating the portion of blood that contains the protein (e.g., using a centrifuge), purifying the protein, submitting the a purified solution of the protein to a calibrated assay (e.g., using marked antibodies), or any other step that may yield the concentration of the protein in the blood sample. In other instances, the protein may be an enzyme, in which case it may be desirable to measure the concentration of the protein through its enzymatic activity level.

One with ordinary skills in the art of medical or veterinary diagnosis is able to recognize the laboratory method steps, and laboratory equipment represented by block 310 for collecting biological sample, extracting the pertinent biomarker, and measuring its level.

As described above in the definition of term "biomarker", the biological data may be any type of data that be involved in diagnosing a specific health affection whether the biological data may be assessed using a biological sample from the subject's body or through observational assessment of symptoms. For example, biological data comprise body temperature (e.g., in fever cases) heart beat rate, the number of siblings or parents having an affection (e.g., in cases of inherited affections), the elapsed time since the first signs of a disease started to show symptoms or any other non-substance related measurement that may be obtained from a patient and that may be considered in a diagnosis. Block 310 represents the tools and equipments necessary for collecting the biological data, which is accessible to one with ordinary skills in the pertinent art.

Block 320 represents a computer system for implementing and executing computer program instructions following the teachings of the methods developed in an embodiment of the invention. The computer system is any analog and/or digital computer capable of being configured to take input data, execute some or all of the method steps of the invention and provide the result of such execution to a user.

The computer system 320 may be a digital computer having a digital processor, a memory, a data transfer bus, a storage medium and any electronic communication means that allows the computer to receive and send data through display and communication to and from users and/or other machines. In embodiments of the invention, the computer may be embedded (as symbolized by block 305) in a device for carrying out medical (or veterinary) tests. Thus, a mobile and/or portable system comprises a device configured to collect the data such as determining the level or one or more biomarker level in a blood sample, and a computer system for carrying the steps of the invention. The device may be enabled with display means such that the results are communicated to a user.

In other embodiments of the invention, the computer 320 may stand alone, such as a computer system that is detached from any particular a device, while being capable of receiving data through direct communication (e.g., user interface), and/or remote communication means (e.g., networked data transfer).

The input data may be any of the biological and non-biological data, described above, that may be entered to the computer automatically through one or more links 332, or through a user interface 334 provided to a user 300. For example, a practitioner 300 may obtain the biological data from the data collection system through one or more communication (or interface links) 330, then enter the data into the computer system through the computer interface 334.

The practitioner may also enter in the computer system further configuration data, such as range boundaries for data discretization, optimization method or any other configuration data to conduct a search for optimal parameters. The computer system comprises program instructions to conduct a search for optimal parameters. Computer system 320 contains program instructions the execution of which allows to discretize new data (e.g., from a patient) compute one or more indices, then compare the new data to previously generated (or stored data) in order to provide a diagnosis.

In embodiments of the invention, a computer program as well as the data for any particular diagnosis method, in computer system 320, may be replicated from one machine to another, thus, allowing the diagnosis programs to be replicated to any number of other machines. For example, in portable blood test devices, a computer program may be configured to process the data and provide fast diagnosis using pre-stored diagnosis parameters.

However, the data acquisition system may be separated and remotely located and may serve the practitioner remotely. For example, the computer program may be implemented on a central unit that may collected biological data from a plurality of data acquisition systems (e.g., using computer networks), and serve client machines with diagnoses as they may be entered remotely. Furthermore, the collection of data from a plurality of client data acquisition system may serve to further refine the diagnosis program as more and more data become available.

Method of Detecting and Differentiating Lymphosarcoma and Inflammatory Bowel Disease An embodiment of the invention targets the diagnosis of cancer and inflammation in a typical patient i.e. showing general symptoms of inflammation while failing to reveal the underlying affection from visible symptoms. Inflammation may be caused by a number of factors including cancer, infection, trauma and many other factors. A method according to the invention may use the measurement of the biomarkers thymidine kinase (TK) and haptoglobin (HP) to distinguish between whether a patient is affected by one and/or the other disease. According to the method steps described in FIG. 1, the development of a diagnosis starts with the specification of one or more target affections, and a set of data (e.g., biomarkers) that will be used in the diagnosis method. Below is a brief introductory description of thymidine kinase and haptoglobin involvement in cancer and inflammation. The details of the mechanisms involved in the variations of the latter biomarkers in the affections in question are beyond the scope of the present disclosure, but are readily available in the scientific literature.

There has been a long standing and studied relationship between cancer and inflammation. The inflammatory response orchestrates host defenses to infection, trauma, toxins, or other tissue damaging events and mediates tissue repair and regeneration. Epidemiological evidence points to a connection between inflammation and a predisposition for the development of cancer, i.e. long-term inflammation leads to the development of dysplasia. Thus, while acute inflammation is normally tightly controlled and part of the healing process, chronic inflammation may be associated with a number of diseases including cancer.

In cancer, there is evidence that inflammation plays an essential role at each stage of the disease (initiation and proliferation), and both tumor and inflammatory cells are able to directly or indirectly either inhibit or stimulate tumor growth. The effectiveness of tumor development has been demonstrated to correlate directly with the degree of the inflammatory reactions, and it seems that there are interactions between the cytokines produced in response to inflammatory reactions and tumor growth and even indications that inflammatory cytokines favor tumor promotion. Furthermore, with the assistance of inflammation, tumor cells infiltrate neighboring tissues, enter into the bloodstream, migrate, and establish remote colonies i.e. metastases.

The inflammatory processes (e.g., triggered by infection, injury, extreme stress etc.) are accompanied by a release of the acute-phase proteins (APP), among which is haptoglobin. Haptoglobin is synthesized in the liver in the most part, and in other organs such as lung, kidney and skin. Once release in the blood stream, haptoglobin binds to hemoglobin, and facilitates the breakdown of hemoglobin.

In cats, where lymphoma is a common cancer, diagnosing Lymphoma is problematic, due to the fact that the symptoms may vary depending on the affected organ. For instance, the symptoms that develop as a result of Lymphoma in cats such as loss of appetite, weight loss, vomiting and diarrhea, that are also typically indicative of Inflammatory Bowel Disease (IBD). Relying on these symptoms alone may lead to a miss-diagnosis of IBD, when the real underlying disease is Lymphoma.

Consequently, mistakenly diagnosing IBD instead of Lymphoma may lead to treatments that typically involve using steroids (e.g., Prednisone). The steroid treatment, although appears to relieve the symptoms, promotes the progression of cancerous cells, thus complicating the detection of the true cause of the symptoms (i.e., lymphoma), and later treatment of lymphoma.

An embodiment of the invention, utilizes haptoglobin presence level in the blood plasma in the revealing of whether the underlying affection, in a cat showing symptoms of disease, is lymphosarcoma or inflammatory bowel disease.

An embodiment of the invention combines a set of biomarkers comprising thymidine kinase. Thymidine kinase has been well studied in both human and veterinary applications. TK is commonly expressed by a wide array of neoplasms, both benign and malignant. Historically, research has been centered on hematopoietic cancers such as leukemia and lymphoma where serum levels of TK reach high concentrations. More recently, TK has been shown to be expressed by a wide array of sarcomas, such as hemangiosarcoma.

Thymidine kinase type 1 (TK) is a cytosolic enzyme involved in DNA synthesis through the so called "salvage pathway" for thymidine biosynthesis, in which deoxythymidine is converted to deoxythymidine monophosphate, leading to its eventual incorporation into DNA. Cellular TK activity is closely correlated with the DNA synthesis phase of the cell cycle. As such, its expression is restricted to proliferating cells, and thus is often more highly expressed in malignant cells, which are characterized by dysregulated proliferation.

In accordance with the method of the invention described in FIG. 1, an embodiment of the invention targets the detection of lymphosarcoma and the differentiation with IBD using two biomarkers. To the latter end, a study involving fifty six (56) cats was conducted to evaluate the dual biomarker method. The appropriate histological testing was carried out to establish whether each subject had cancer, IBD or was apparently healthy. Thus in the fifty six (56) cats, fifteen (15) were diagnosed with lymphosarcoma and eleven (11) has IBD. The rest of cats (i.e. 30) were apparently healthy.

The goal is to establish a method, in accordance with an embodiment of the invention, for classifying subjects into two groups: one group comprising subjects that have cancer versus the rest of the subjects that are unaffected by cancer even as they show symptoms of inflammation (e.g., due to IBD). Thus, subsequently by measuring the level of the biomarkers in a subject, the method allows a practitioner to use the results as a diagnosis of current health status and/or as a predictor of the risk that a subject would eventually develop cancer.

The measurement of thymidine kinase enzymatic activity in samples of blood plasma is described in U.S. Pat. No. 8,097,432 B2, which is included herewith in its entirety by reference. In brief, a blood plasma is separated from a sample of blood to be tested for TK activity. The plasma is introduced into a solution containing an analog of deoxythymidine nucleotide and a phosphate donor. The product of the enzymatic activity is then measured using an immunoassay.

The measurement of haptoglobin may be carried out using any available method for extracting and measuring protein concentration in a bodily fluid or tissue. The latter methods comprise using centrifugal force, electrophoresis, chromatography, immuno-binding assays and any available method for measuring the concentration of a protein.

Using TK and haptoglobin (HP) in the latter study, and in accordance with the invention as described by formula (1) and FIG. 1, a two-parameter neoplasia index may be computed, by applying equation (1), as follows:

$$N_2 = a_2 \cdot dTK + b_2 \cdot dHP \quad (2)$$

Where "$N_2$" denotes the Neoplasia index in a two (2) parameter model using TK and HP, and where "$a_2$" and "$b_2$" denote the coefficients associated with TK and CRP, respectively. "dTK" and "dCRP" denote the discrete score value matched with a range of TK level and CRP level, respectively. As described above, TK level may be represented by the level of its enzymatic activity, whereas HP may be represented by its mass (or moles) per volume of blood plasma.

As described above, the level of the biomarkers was measured and discretized. A discrete score assigned to ranges of the levels for each biomarker. Table 1 shows the detail of the discretization scores corresponding to ranges for each of TK and CRP level.

TABLE 1

Discrete scores for TK and HP ranges

| TK (U/L) | HP (mg/dL) | Score |
|---|---|---|
| 0 to 2.9 | 0 to 94 | 0 |
| 3.0 to 8.3 | 95 to 149 | 1 |
| 8.4 or greater | 150 or greater | 2 |

Figure 4:
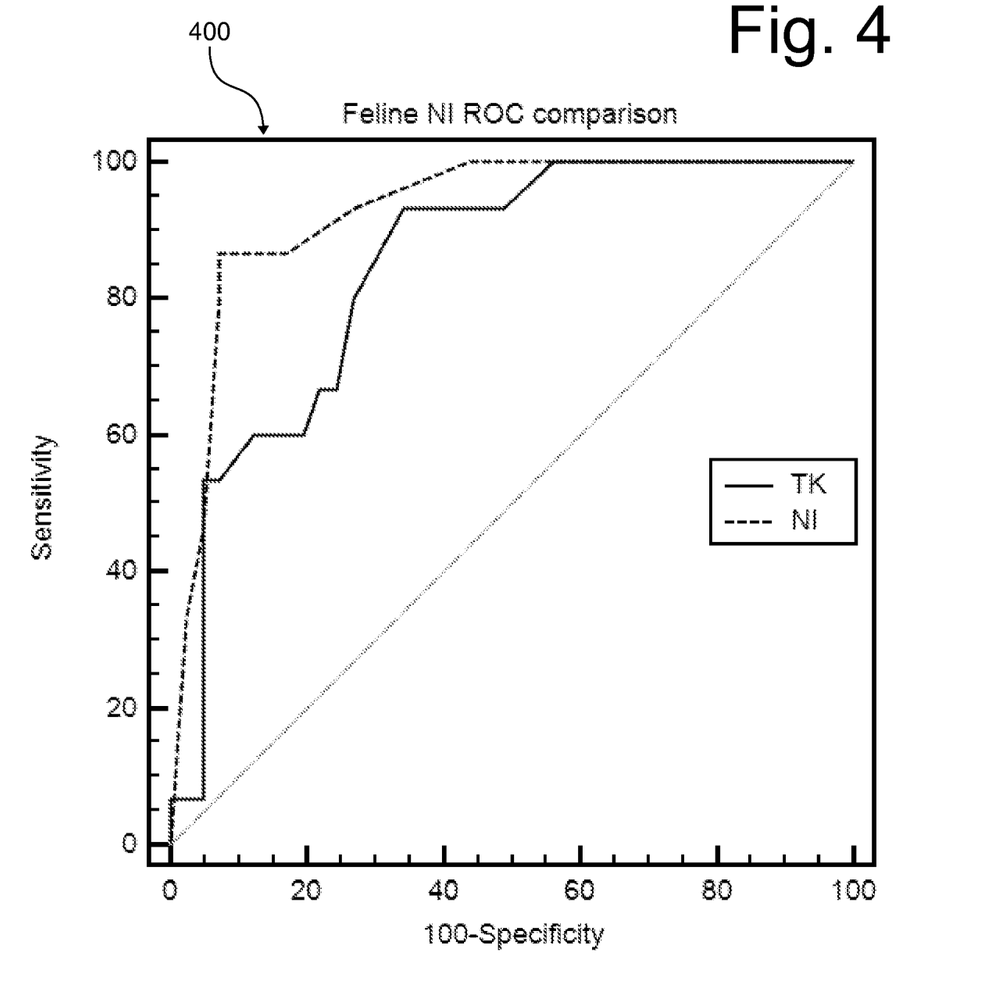
FIG. 4 shows plots of the Receiver Operating Characteristic (ROC) curves Sensitivity vs. one hundred (100) minus Specificity using TK alone and the two-biomarker implementation of the invention following confirmation of cancer in a subset of subjects.

In the latter two-biomarker method, the coefficients "$a_2$" and "$b_2$" of formula (2) are given the values two (2) and one point five (1.5), respectively. With the latter parameters and the discretization values of table 1, the index value for any data set (of TK and HP) ranges between FIG. 4 shows plots of the Receiver Operating Characteristic (ROC) curves Sensitivity vs. one hundred (100) minus Specificity using TK alone and the two-biomarker implementation of the invention following confirmation of cancer in a subset of subjects. Plot 400 shows the plot of the ROC curve for TK (solid line). The area under the curve (AUC) is 0.847 (or 84.7%). At value level of TK of 7.6 U/l or greater, the Sensitivity is 0.53 (or 53%%), and the Specificity is 0.93 (or 93%). The dashed line represents the results obtained with using the neoplasia index in accordance with formula 2 with discrete values in table 1. The AUC for NI in plot 400 is 0.928 (or 92.8%). At a value 3.5 or greater the Sensitivity is 0.87 (or 87%) and Specificity is 0.93 (or 93%). The results, as shown in FIG. 4, confirm that the predictive power of the method is greater when using the two-biomarker neoplasia index than by using TK alone to diagnose lymphosarcoma in cats. The difference between the results obtained with TK alone as compared with the values obtained using the neoplasia index is statistically significant (at P=0.03).

Figure 5A:
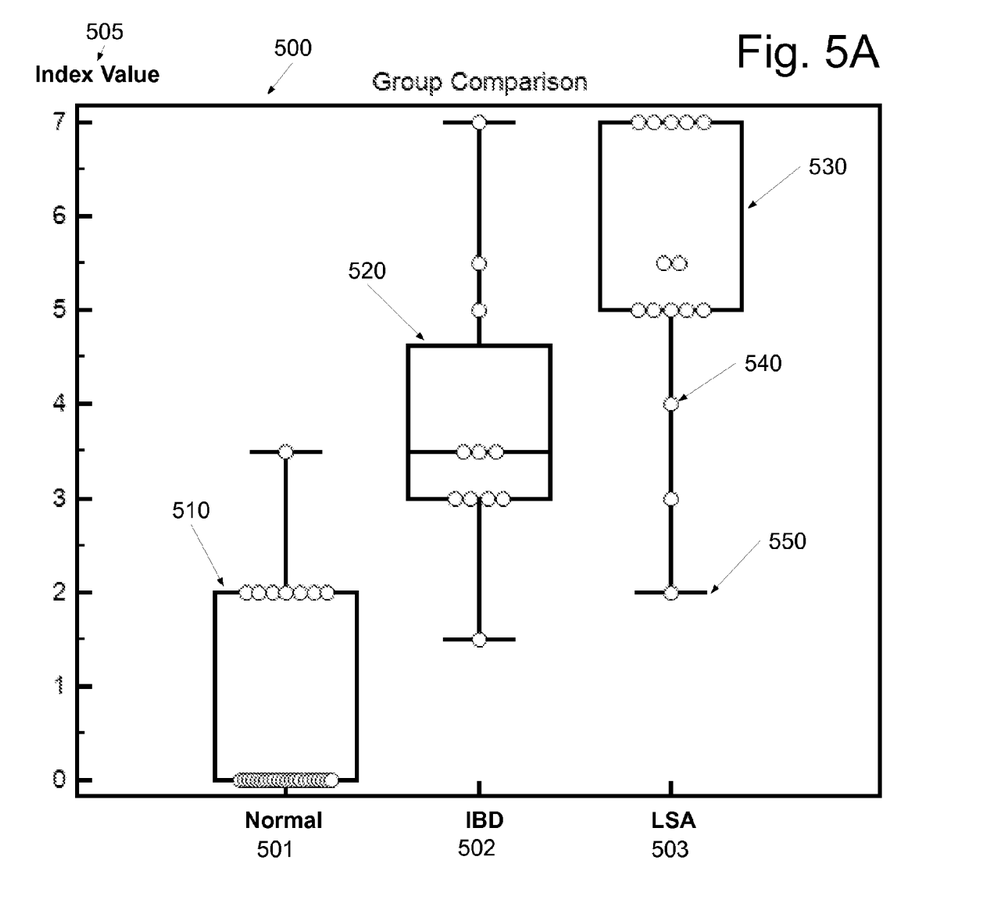
FIG. 5A is a chart presenting the results of the neoplasia index method in accordance with an embodiment of the invention.

FIG. 5A is a chart presenting the results of the neoplasia index method in accordance with an embodiment of the invention. Chart 500 shows the values of neoplasia index 505 for each group: normal 501, IBD-affected subjects 502 and LSA-affected 503 subjects. Each circle 540 represents the index value of an individual subject in the cohort. Each box (e.g., 510, 520 and 530) represents the spread around the median value for its respective group. The vertical bars (e.g., 550) represent the range of values for each group.

FIG. 5A graphically illustrates that the neoplasia index values form ranges that maps to the status of the underlying affection of the subjects, even though there is a some overlapping of the ranges. As shown in the statistical analysis (see above) and FIG. 5, the method of the invention allows for segregating individual subjects on the basis of there neoplasia index values while minimizing the error level for such segregation.

Figure 5B:
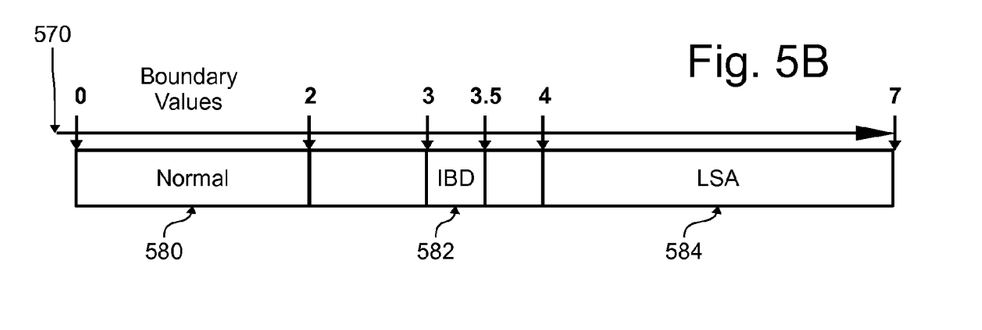
FIG. 5B graphically represents the predefined ranges for determining a subject as having a high probability of having lymphosarcoma, having inflammatory bowel disease or being normal in accordance with an embodiment of the invention.

FIG. 5B graphically represents the predefined ranges for determining a subject as having a high probability of having lymphosarcoma, having inflammatory bowel disease or being normal in accordance with an embodiment of the invention. Using formula (2) to calculate the neoplasia index with the coefficients "$a_2$" and "$b_2$" given the values two (2) and one point five (1.5), respectively, the possible values of the index are between zero (0) and seven (7). FIG. 5B shows an index scale 570, and the health affections "Normal" 580, IBD-affected 582 and lymphosarcoma-affected 584. The neoplasia index shows range boundaries that allow a practitioner to utilize the predefined ranges in a diagnosis. When a subject's neoplasia index is between zero (0) and two (2), the predefined index ranges indicate that the subject has a high probability of being normal; when a subject's neoplasia index is between three (3) and three and half (3.5), the predefined index ranges indicate that the subject has a high probability of having inflammatory vowel disease; and when a subject's neoplasia index is between four (4) and seven (7), the predefined index ranges indicate that the subject has a high probability of having lymphosarcoma.

Thus, a method and system for selecting a set of biomarkers and developing a method of use for detecting lymphosarcoma and differentiating between the cancer-affected versus IBD-affected and normal subjects, in order to help a practitioner interpret the biomarkers data.

The claimed invention is:

1. A method for diagnosing lymphosarcoma in felines comprising the steps of:
    obtaining a serum portion of a blood sample from a feline subject;
    obtaining the activity level of thymidine kinase in said serum portion, further comprising obtaining a first discrete value wherein said first discrete value is assigned a value zero (0) when the activity level of thymidine kinase is less than 2.9 U/l, said first discrete value is assigned a value of one (1) when the activity level of thymidine kinase is between about 3 U/l and about 8.3 U/l, and said first discrete value is assigned a value of two (2) when the activity level of thymidine kinase is greater than about 8.4 U/l;
    obtaining the concentration of haptoglobin in said serum portion, further comprising obtaining a second discrete value wherein said second discrete value is assigned the value zero (0) when said concentration of haptoglobin is less than 94 mg/dl, said second discrete value is assigned the value one (1) when the concentration of haptoglobin is between about 95 mg/dl and about 149 mg/dl, said second discrete value is assigned the value two (2) when the concentration of haptoglobin is greater than about 150 mg/dl;
    computing an index value by adding said first discrete value multiplied by a thymidine weighing coefficient of value 2 and said second discrete value multiplied by a haptoglobin weighing coefficient of value 1.5;
    determining that said feline subject has a high probability of being normal when said index value is within zero (0) and two (2), said feline subject has a high probability of having inflammatory bowel disease when said index value is between three (3) and three and a half (3.5) and said feline subject has a high probability of having lymphosarcoma if said index value is between four (4) and seven (7).

* * * * *